(12) United States Patent
Grossman (10) Patent No.: US 6,395,486 B1
(45) Date of Patent: May 28, 2002

(54) PROBE/MOBILITY MODIFIER COMPLEXES FOR MULTIPLEXNUCLEIC ACID DETECTION

(75) Inventor: Paul D. Grossman, Foster City, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/522,640

(22) Filed: Mar. 10, 2000

Related U.S. Application Data (60) Provisional application No. 60/124,386, filed on Mar. 15, 1999.

(51) Int. Cl.[7] ............................. C12Q 1/68; C12P 19/34
(52) U.S. Cl. .......................... 435/6; 435/91.2; 536/23.1
(58) Field of Search .................... 435/6, 91.2; 536/23.1

(56) References Cited

U.S. PATENT DOCUMENTS

| 5,514,543 A | * | 5/1996 | Grossman et al. ............. 435/6 |
| 5,630,924 A | | 5/1997 | Fuchs et al. |
| 5,777,096 A | | 7/1998 | Grossman et al. |

FOREIGN PATENT DOCUMENTS

| WO | WO93/20236 | 10/1993 |
| WO | WO93/25563 | 12/1993 |
| WO | WO97/31256 | 8/1997 |
| WO | WO97/42348 | 11/1997 |
| WO | WO97/45559 | 12/1997 |
| WO | WO98/38335 | 9/1998 |
| WO | PCT/US00/00972 | 1/2000 |

OTHER PUBLICATIONS

Grossman et al., 1994, "High–Density Multiplex Detection of Nucleic Acid Sequences: Oligonucleotide Ligation Assay and Sequence–Coded Separation," *Nucleic Acids Research* 22(21):4527–4534.

Pastinen T. et al., "Minisequencing: A Specific Tool for DNA Analysis and Diagnostics on Oligonucleotide Arrays," *Genome Research*, 7:606–614, 1997.

Perry–O'Keefe H., et al. "Peptide nucleic acid pre–gel hybridization: An alternate to Southern hybridization," *Proc. Natl. Acad. Sci. USA*, vol. 93, pp. 14670–14675, Dec. 1996.

Shoemaker D.D., et al. "Quantitative phenotypic analysis of yeast deletion mutants using a highly parallel molecular bar–coding strategy," *Nature Genetics*, vol. 14, pp. 450–456, Dec. 1966.

\* cited by examiner

*Primary Examiner*—W. Gary Jones
*Assistant Examiner*—Juliet C. Einsmann
(74) *Attorney, Agent, or Firm*—Paul D. Grossman (57) ABSTRACT

Compositions and methods for the analysis of multiple nucleic acid target sequences are disclosed. The compositions comprise a probe comprising a target-specific portion for sequence-specific hybridization to a target nucleic acid sequence, and a tag; and a mobility-modifier comprising a tail and a tag complement for binding to the tag. The associated methods generally comprise the steps of providing a sample potentially containing one or more target nucleic acid sequences; providing one or more probes, each probe comprising a target-specific portion and a tag; providing one or more mobility modifiers, each mobility modifier comprising a tag complement and a tail; contacting the probe(s) and the target nucleic acid sequence(s) under conditions effective for sequence-dependent hybridization of the probe(s) and the target nucleic acid sequence(s); contacting the probe(s) and the mobility-modifier(s) under conditions suitable for selectively binding the probe(s) to the mobility modifier(s), thereby forming one or more a probe/mobility modifier complex(s); and analyzing the probe/mobility modifier complex(s) using a mobility-dependent analysis technique.

14 Claims, 2 Drawing Sheets

PROBE/MOBILITY MODIFIER COMPLEXES FOR MULTIPLEXNUCLEIC ACID DETECTION

This application claims priority to provisional application No. 60/124,386. Mar. 13, 1999 was added.

FIELD OF THE INVENTION

This invention relates to methods and compositions useful for the analysis of nucleic acid sequences. In particular, the invention provides methods and compositions useful for the analysis of mixtures of multiple nucleic acid sequences.

BACKGROUND

Nucleic acid analysis techniques capable of large-scale multiplex analysis of a plurality of polymorphic loci are needed for a variety of practically important applications, e.g., for the identification of individuals, e.g., paternity testing or in forensic analysis, for organ transplant donor-recipient matching, for genetic disease diagnosis, prognosis and genetic counseling, for characterization of infectious agents, and for the study of oncogenic mutations. Many of these applications depend on the ability to discriminate single-nucleotide differences in a target nucleic acid sequence at a multiplicity of loci.

One solution to the problem of multiplex analysis of nucleic acids is to use arrays of different-sequence nucleic acids attached to a solid support, where the sequence of the attached nucleic acids are related to their location in the array (e.g., Kucherlapti and Childs, *Nature Genetics*, 21: 15–19 (1999); Lipshutz et al., *Nature Genetics*, 21: 20–24 (1999)). However, nucleic acid arrays have several significant practical drawbacks including (1) issues associated with the fabrication of arrays, e.g., the expense and complexity of the fabrication and testing of arrays, e.g., by in situ synthesis or spotting; (2) characterization of arrays once they are fabricated, e.g., confirmation that the proper sequence is located at the proper location; (3) the integrity the nucleic acid at each array location, e.g., there may be intra-strand cross-linking and/or multiple constraining contacts between the solid support and the bound nucleic acid; and (4) difficulties associated with detecting hybridization events on a solid support, e.g., fluorescence background and/or non-specific binding of a labeled entity to the support.

In an alternative approach, multiple probes are analyzed by electrophoretically separating probes that include mobility-modifying tails that correlate a particular probe with a particular mobility address (e.g., Grossman et al., *Nucl. Acids Res.*, 22: 4527–4534 (1994); Grossman et al, U.S. Pat. No. 5,624,800). However, this approach has the drawback of requiring the synthesis of a large number of tailed probes.

Thus, there remains a continuing need for a nucleic acid analysis technique that permits highly multiplexed analysis without the drawbacks associated with nucleic acid arrays or with existing mobility-based methods.

SUMMARY

The present invention is directed towards methods and compositions useful for the multiplex analysis of nucleic acids.

In a first aspect, the present invention provides a binary composition for detecting one or more target nucleic acid sequences in a mixture. The binary composition includes a probe having a target-specific portion for sequence-specific hybridization to a target nucleic acid sequence, and a tag. The binary composition further includes a mobility modifier having a tail and a tag complement for binding to the tag. When the probe and the mobility modifier are bound through the tag and tag complement, a probe/mobility modifier complex is formed. In a preferred embodiment, the probe comprises a polynucleotide.

In a second aspect, the present invention provides a method for detecting one or more target nucleic acid sequences present in a sample. In the method, a sample potentially containing one or more target nucleic acid sequences is contacted with one or more probes under conditions effective for sequence-dependent hybridization of the probe and the target nucleic acid sequence, where each probe includes a target-specific portion and a tag. Next, the hybridized probe is treated to form a modified probe, where the treatment is effective to distinguish probes that have bound to the target nucleic acid from those that have not. Before or after the probes are contacted with the target nucleic acid, the probe are contacted with one or more mobility-modifiers to form a probe/mobility modifier complex, each mobility modifier having a tag complement for binding selectively to the tag of an associated probe, and a tail. Finally, the probe/mobility modifier complex is analyzed using a mobility-dependent analysis technique.

The present invention will become better understood with reference to the following written description, drawings, and appended claims.

DETAILED DESCRIPTION OF THE PREFERRED EMBODIMENTS

Reference will now be made in detail to the preferred embodiments of the present invention, examples of which are illustrated in the accompanying drawings. While the invention will be described in conjunction with these preferred embodiments, it will be understood that the invention is not intended to be limited to those embodiments. On the contrary, the invention is intended to cover alternatives, modifications, and equivalents of these preferred embodiments that may be included within the invention as defined by the appended claims.

I. Definitions

Unless stated otherwise, the following terms and phrases as used herein are intended to have the following meanings:

The term "label" refers to a moiety that, when attached to the compositions of the invention, render such compositions detectable using known detection means, e.g., spectroscopic, photochemical, radioactive, biochemical, immunochemical, enzymatic or chemical means. Exemplary labels include but are not limited to fluorophores, chromophores, radioisotopes, spin labels, enzyme labels and chemiluminescent labels. Such labels allow direct detection of labeled compounds by a suitable detector, e.g., a fluorescence detector. In addition, such labels include components of multicomponent labeling schemes, e.g., a system in which a ligand binds specifically and with high affinity to a detectable anti-ligand, e.g., a labeled antibody binds to its corresponding antigen.

The term "hybridization enhancer" means moieties that serve to enhance, stabilize, or otherwise positively influence hybridization between two polynucleotides, e.g. intercalators (e.g., U.S. Pat. No. 4,835,263), minor-groove binders (e.g., U.S. Pat. No. 5,801,155), and cross-linking functional groups.

"Linking group" means a moiety capable of reacting with a "complementary functionality" to form a "linkage." A linking group and its associated complementary functionality is referred to herein as a "linkage pair." Preferred linkage pairs include a first member selected from the group isothiocyanate, sulfonyl chloride, 4,6-dichlorotriazinyl, succinimidyl ester, or other active carboxylate, and a second member that is amine. Preferably a first member of a linkage pair is maleimide, halo acetyl, or iodoacetamide whenever the second member of the linkage pair is sulfhydryl. (e.g., R. Haugland, *Molecular Probes Handbook of Fluorescent Probes and Research Chemicals*, Molecular probes, Inc. (1992)). In a particularly preferred embodiment, the first member of a linkage pair is N-hydroxysuccinimidyl (NHS) ester and the second member of the linkage pair is amine, where, to form an NHS ester, a carboxylate moiety is reacted with dicyclohexylcarbodiimide and N-hydroxysuccinimide.

The term "Watson/Crick base-pairing" refers to a pattern of specific pairs of nucleotides, and analogs thereof, that bind together through sequence-specific hydrogen-bonds, e.g. A pairs with T and U, and G pairs with C.

The term "nucleoside" refers to a compound comprising a purine, deazapurine, or pyrimidine nucleobase, e.g., adenine, guanine, cytosine, uracil, thymine, 7-deazaadenine, 7-deazaguanosine, and the like, that is linked to a pentose at the 1'-position. When the nucleoside base is purine or 7-deazapurine, the pentose is attached to the nucleobase at the 9-position of the purine or deazapurine, and when the nucleobase is pyrimidine, the pentose is attached to the nucleobase at the 1-position of the pyrimidine, (e.g., Komberg and Baker, *DNA Replication*, 2nd Ed. (Freeman, San Francisco, 1992)). The term "nucleotide" as used herein refers to a phosphate ester of a nucleoside, e.g., a triphosphate ester, wherein the most common site of esterification is the hydroxyl group attached to the C-5 position of the pentose. The term "nucleoside/tide" as used herein refers to a set of compounds including both nucleosides and nucleotides.

The term "polynucleotide" means polymers of nucleotide monomers, including analogs of such polymers, including double and single stranded deoxyribonucleotides, ribonucleotides, α-anomeric forms thereof, and the like. Monomers are linked by "internucleotide linkages," e.g., phosphodiester linkages, where as used herein, the term "phosphodiester linkage" refers to phosphodiester bonds or bonds including phosphate analogs thereof, including associated counterions, e.g., $H^+$, $NH_4^+$, $Na^+$, if such counterions are present. Whenever a polynucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes deoxythymidine, unless otherwise noted.

"Analogs" in reference to nucleosides/tides and/or polynucleotides comprise synthetic analogs having modified nucleobase portions, modified pentose portions and/or modified phosphate portions, and, in the case of polynucleotides, modified internucleotide linkages, as described generally elsewhere (e.g., Scheit, *Nucleotide Analogs* (John Wiley, New York, (1980); Englisch, *Angew. Chem. Int. Ed. Engl.* 30:613–29 (1991); Agrawal, *Protocols for Polynucleotides and Analogs*, Humana Press (1994)). Generally, modified phosphate portions comprise analogs of phosphate wherein the phosphorous atom is in the +5 oxidation state and one or more of the oxygen atoms is replaced with a non-oxygen moiety, e.g., sulfur. Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Exemplary modified nucleobase portions include but are not limited to 2,6-diaminopurine, hypoxanthine, pseudouridine, C-5-propyne, isocytosine, isoguanine, 2-thiopyrimidine, and other like analogs. Particularly preferred nucleobase analogs are iso-C and iso-G nucleobase analogs available from Sulfonics, Inc., Alachua, Fla. (e.g., Benner, et al., U.S. Pat. No. 5,432,272). Exemplary modified pentose portions include but are not limited to 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, bromo and the like. Modified internucleotide linkages include phosphate analogs, analogs having achiral and uncharged intersubunit linkages (e.g., Sterchak, E. P., et al., *Organic Chem,* 52:4202 (1987)), and uncharged morpholino-based polymers having achiral intersubunit linkages (e.g., U.S. Pat. No. 5,034,506). A particularly preferred class of polynucleotide analogs where a conventional sugar and internucleotide linkage has been replaced with a 2-aminoethylglycine amide backbone polymer is peptide nucleic acid (PNA) (e.g., Nielsen et al., *Science,* 254:1497–1500 (1991); Egholm et al., *J. Am. Chem. Soc.,* 114: 1895–1897 (1992)).

As used herein the term "primer-extension reagent" means a reagent comprising components necessary to effect an enzymatic template-mediated extension of a polynucleotide primer. Primer extension reagents include (1) a polymerase enzyme, e.g., a thermostable DNA polymerase enzyme such as Taq polymerase; (2) a buffer; (3) one or more chain-extension nucleotides, e.g., deoxynucleotide triphosphates, e.g., deoxyguanosine 5'-triphosphate, 7-deazadeoxyguanosine 5'-triphosphate, deoxyadenosine 5'-triphosphate, deoxythymidine 5'-triphosphate, deoxycytidine 5'-triphosphate; and, optionally in the case of Sanger-type DNA sequencing reactions, (4) one or more chain-terminating nucleotides, e.g., dideoxynucleotide triphosphates, e.g., dideoxyguanosine 5'-triphosphate, 7-deazadideoxyguanosine 5'-triphosphate, dideoxyadenosine 5'-triphosphate, dideoxythymidine 5'-triphosphate, and dideoxycytidine 5'-triphosphate.

"Mobility-dependent analysis technique" means an analysis technique based on differential rates of migration between different analyte species. Exemplary mobility-dependent analysis techniques include electrophoresis, chromatography, sedimentation, e.g., gradient centrifugation, field-flow fractionation, multi-stage extraction techniques and the like.

II. Target Nucleic Acid Sequence

A target nucleic acid sequence for use with the present invention may be derived from any living, or once living, organism, including but not limited to prokaryote, eukaryote, plant, animal, and virus. The target nucleic acid sequence may originate from a nucleus of a cell, e.g., genomic DNA, or may be extranuclear nucleic acid, e.g., plasmid, mitochondrial nucleic acid, various RNAs, and the like. The target nucleic acid sequence may be first reverse-transcribed into cDNA if the target nucleic acid is RNA. Furthermore, the target nucleic acid sequence may be present in a double stranded or single stranded form.

A variety of methods are available for obtaining a target nucleic acid sequence for use with the compositions and methods of the present invention. When the target nucleic acid sequence is obtained through isolation from a biological matrix, preferred isolation techniques include (1) organic extraction followed by ethanol precipitation, e.g., using a phenol/chloroform organic reagent (e.g., Ausubel et al.eds., *Current Protocols in Molecular Biology Volume* 1, Chapter 2, Section I, John Wiley & Sons, New York (1993)), preferably using an automated DNA extractor, e.g., the Model 341 DNA Extractor available from PE Applied Biosystems (Foster City, Calif.); (2) stationary phase adsorption methods (e.g., Boom et al., U.S. Pat. No. 5,234,809; Walsh et al., *Biotechniques* 10(4): 506–113 (1991)); and (3) salt-induced DNA precipitation methods (e.g., Miller et al., *Nucleic Acids Research*,16(3): 9–10 (1988)), such precipitation methods being typically referred to as "salting-out" methods. Optimally, each of the above isolation methods is preceded by an enzyme digestion step to help eliminate unwanted protein from the sample, e.g., digestion with proteinase K, or other like proteases.

To increase the sensitivity and specificity of the method of the invention, preferably the target nucleic acid sequence is amplified prior to performing the method using a suitable nucleic acid amplification procedure. Such amplification may be linear or non-linear, e.g., exponential. Exemplary amplification procedures include, but are not limited to, the polymerase chain reaction (PCR) (e.g., Mullis et al., U.S. Pat. Nos. 4,683,195, 4,683,195, and 4,683,202), the self-sustained sequence replication reaction (3SR) (e.g., Gingeras et al., *Ann. Biol. Clin.,* 48: 498–501 (1990)), the ligation amplification reaction (LAR) (Wu and Wallace, *Genomics,* 4: 560–569 (1989)), the ligase chain reaction (LCR) (e.g., Winn-Deen, E., et al., *Clin. Chem.,* 37: 1522 (1991)), and the nucleic acid sequence based amplification reaction (NASBA) (e.g., van Gemen et al., *J Virol. Methods,* 43: 177–188 (1993)). In a particularly preferred embodiment, amplification of the target nucleic acid sequence is accomplished using PCR. Generally, the PCR consists of an initial denaturation step that separates the strands of a double stranded nucleic acid, followed by the repetition of (1) an annealing step, which allows two amplification primers to anneal specifically to positions flanking a target nucleic acid sequence; (2) an extension step which extends the primers in a 5'→3' direction thereby forming an amplicon nucleic acid complementary to a portion of the target nucleic acid sequence located between the primers, and (3) a denaturation step which causes the separation of the amplicon. Each of the above steps may be conducted at a different temperature, where the temperature changes may be effected using an automated thermocycler (e.g., PE Applied Biosystems, Foster City, Calif.). In a particularly preferred embodiment, multiple loci of the target nucleic acid sequence are amplified by multiplex PCR, thereby allowing multiple regions of a target nucleic acid sequence to be investigated simultaneously (e.g., Chamberlain et al., *Nucleic Acids Research,* 16: 11141–11156 (1988); *PCR Primer: A Laboratory Manual,* Dieffenbach and Dveksler, eds., CSHL Press (1995); Caskey et al., U.S. Pat. No. 5,582,989).

III. Binary Compositions

This section describes several preferred embodiments of binary compositions designed for use in the methods of the present invention. In a typical case, the binary compositions are part of a composition containing a plurality of probes and associated mobility modifiers for use in detecting a plurality of target nucleic acid sequences, according to a variety of methods, several of which are described herein.

Figure 1:
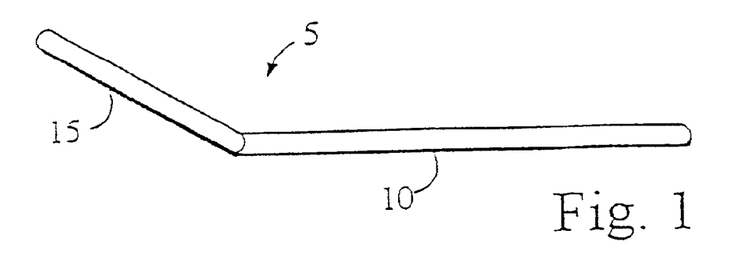
FIG. 1 shows a schematic representation of a probe according to the present invention.
Figure 2:
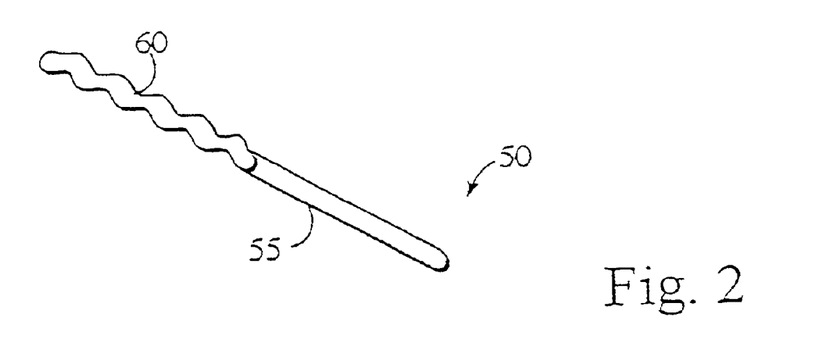
FIG. 2 shows a schematic representation of a mobility modifier according to the present invention.
Figure 3:
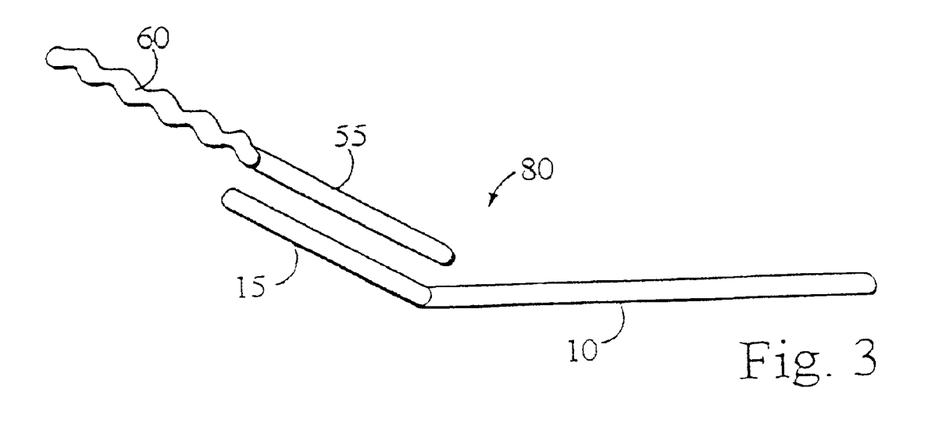
FIG. 3 shows a schematic representation of a probe/mobility modifier complex of the present invention.

As shown schematically in FIGS. 1, 2 and 3, the binary composition of the present invention comprises (1) a probe 5 comprising a target-specific portion 10 for sequence-specific hybridization to a target nucleic acid sequence, and a tag portion 15, and (2) a mobility-modifier 50 comprising a tag complement 55 for binding to the tag portion 15 of the probe, and a tail 60 for effecting a particular mobility in a mobility-dependent analysis technique. According to an important feature of the invention, when a probe 5 and a mobility-modifier 50 having complementary tag 15 and tag complement 55 portions are contacted, a stable probe/mobility-modifier complex 80 is formed.

As stated above, the probe 5 of the binary composition includes a target-specific portion 10 for sequence-specific hybridization to a target nucleic acid sequence, and a tag portion 15 for binding to a tag complement 55 of a mobility modifier 50.

The target-specific portion 10 of the probe may be any entity capable of sequence-specific binding to a target nucleic acid sequence, either in a double stranded or single stranded form, where, preferably, such sequence-specific binding is able to discriminate between target nucleic acid sequences differing by as little as a single nucleotide, or nucleotide equivalent. Generally, the term "hybridization" or "annealing" will be used to describe such sequence-specific binding between a probe and a target nucleic acid sequence. Target-specific portions may be designed for sequence specific binding to a single-stranded target nucleic acid sequence through Watson-Crick base pairing, or sequence-specific binding to a double-stranded target nucleic acid sequence through Hoogstien binding sites in a major groove of a duplex nucleic acid (e.g., Kornberg, A., et al., *DNA Replication,* pp 46–47, W.H. Freeman and Co., New York (1992)), or any other sequence-specific binding or hybridization mechanism. Preferably, the target-specific portion of a probe will interact with a number of nucleotides in a target nucleic acid sequence large enough to unambiguously identify a unique target nucleic acid sequence, while at the same time small enough to maintain an ability to discriminate between target nucleic acid sequences differing by as little as a single nucleotide.

Preferred target-specific portions include but are not limited to antibodies having specificity for a particular nucleic acid sequence, small-molecule synthetic ligands having nucleic acid sequence-recognition properties (e.g., White et al., *Nature,* 391: 468–471 (1998); Kielkopf et al., *Nat. Struct. Biol.,* 5(2): 104–109; Becker et al., *J. Am. Chem. Soc.,* 101(13): 3664–6 (1979)), polynucleotides, and the like, including combinations of such structures.

Particularly preferred target-specific portions comprise polynucleotides. Typically, when a target-specific portion of a probe is a polynucleotide, the target-specific portion will have a size such that it interacts with about 10 to 40 nucleotides of a target nucleic acid sequence, more preferably about 15 to 30 nucleotides. In certain circumstances, in order to facilitate polymerase-mediated extension of the probe, the target-specific portion includes a 3'-end having an —OH group or other moiety that allows polymerase-mediated incorporation of a nucleotide onto the 3'-end of the probe, or allows enzymatic or chemical ligation of the probe to a neighboring polynucleotide.

A particularly preferred polynucleotide analog suitable as a target-specific portion of a probe (as well as other portions of the binary compositions) is PNA. PNA is preferred because it offers Watson-Crick target-sequence specificity, strong target-probe affinity, e.g., a high melting temperature relative to similarly-sized conventional phosphodiester polynucleotide, the ability to bind a target nucleic acid sequence in both duplex and triplex configurations, and the ability to bind to a target nucleic acid sequence in both a parallel-and anti-parallel orientation (e.g., co-pending U.S. patent application titled "Binary Probe and Clamp Composition and Methods for Target Hybridization Detection," by K. Livak, M. Egholm and M. Hunkapiller, filed Jan. 15, 1999).

The tag portion 15 of a probe 5 of the present invention may be any entity capable of binding to, and forming a complex with, a tag-complement portion 55 of a mobility modifier 50. Additionally, preferred tag and tag-complements should form a complex that (1) is stable under conditions typically used in nucleic acid analysis methods, e.g., aqueous, buffered solutions at room temperature; (2) is stable under mild nucleic-acid denaturing conditions; and (3) does not adversely effect a sequence specific binding of a target-specific portion of a probe with a target nucleic acid sequence. In addition, tags and tag complements of the invention should accommodate sets of distinguishable tags and tag complements such that a plurality of different probes and associated mobility modifiers may be present in the same reaction volume without causing cross-interactions among the tags, tag complements, target nucleic acid sequence and target-specific portions of the probes. Methods for selecting sets of tag sequences that minimally cross hybridize are described elsewhere (e.g., Brenner and Albrecht, PCT Patent Application No. WO 96/41011).

Exemplary tags and/or tag complements include but are not limited to antibodies and associated antigen or hapten, receptors and associated ligands, avidin (or streptavidin) and biotin, and polynucleotide sequences and their complementary sequences.

In a preferred embodiment, the tag and tag complement are each polynucleotide. In a preferred polynucleotide tag or tag complement, the tags and complements are rendered non-extendable by a polymerase, e.g., by including sugar modifications such as a 3'-phosphate, a 3'-acetyl, a 2'-3'-dideoxy, a 3'-amino, and a 2'-3' dehydro.

A particularly preferred polynucleotide tag and tag complement pair comprises a tag that is a conventional synthetic polynucleotide, and a tag complement that is PNA. Where the PNA tag complement has been designed to form a triplex structure with a tag, the tag complement may include a "hinge" region in order to facilitate triplex binding between the tag and tag complement. In a more preferred embodiment, tag and tag complement sequences comprise repeating sequences. Such repeating sequences in the tag and tag complement are preferred by virtue of their (1) high binding affinity, (2) high binding specificity, and (3) high solubility. A particularly preferred repeating sequence for use as a duplex-forming tag or tag complement is $(CAG)_n$, where the three base sequence is repeated from about 1 to 10 times (e.g., Boffa, et al., *PNAS (USA)*, 92:1901–05 (1995); Wittung, et al., *Biochemistry*, 36:7973–79 (1997)). A particularly preferred repeating sequence for use as a triplex-forming tag or tag complement is $(TCC)_n$.

PNA and PNA/DNA chimera molecules can be synthesized using well known methods on commercially available, automated synthesizers, with commercially available reagents (e.g., Dueholm, et al., *J. Org. Chem.*, 59:5767–73 (1994); Vinayak, et al., *Nucleosicles & Nucleotides*, 16:1653–56 (1997)).

When a tag portion is a polynucleotide, the tag may comprise all, part, or none of the target-specific portion of the probe. In some embodiments of the invention, the tag may consist of some or all of the target-specific portion of the probe. In other embodiments of the invention, the tag does not comprise any portion of the target-specific portion of the probe.

Tags 15 may be attached to target-specific portions 10 of probes using any chemically stable linkage, where the choice of linkage chemistry will depend on the nature of the tag and target-specific portions of the probe. In one preferred embodiment, the linkage is formed by the reaction of a primary or secondary amino moiety with a "complementary functionality." Preferably, the complementary functionality is isothiocyanate, isocyanate, acyl azide, N-hydroxysuccinimide (NHS) ester, sulfonyl chloride, aldehyde or glyoxal, epoxide, carbonate, aryl halide, imidoester, carbodiumide, anhydride, 4,6-dichlorotriazinylamine, or other active carboxylate (e.g., Hermanson, *Bioconjugate Techniques*, Academic Press (1996)). In a particularly preferred embodiment, the complementary functionality is an activated NHS ester which reacts with the amine of the substituted propargylethoxyamido nucleoside of the invention, where to form the activated NHS ester, a carboxylate complementary functionality is reacted with dicyclohexylcarbodiimide and N-hydroxysuccinimide to form the NHS ester (Khanna, et al., U.S. Pat. No. 4,318,846 (1988); Kasai, et al., *Anal. Chem.*, 47: 34037 (1975)).

One particularly preferred linkage well suited for the case where both a target specific portion and a tag of a probe are polynucleotide comprised incorporating 1,3-propanediol or 1,4-anhydro-2-deoxy-D-ribotol subunits between the tag and target complementary portions of the probe (e.g., Gade et al., *GATA*, 10(2): 61–65 (1993); Ugozzoli et al., *GATA*, 9: 107–112 (1992)). In another preferred embodiment in which both the target-specific portion and the tag portion of a probe are polynucleotide, the target-specific portion and the tag portion are linked through internucleotide linkages making up the polynucleotide itself.

The mobility modifier 50 of the binary composition of the present invention comprises a tag complement 55 portion for binding to the tag portion 15 of the probe, and a tail 60 for effecting a particular mobility in a mobility-dependent analysis technique.

The tail portion of a mobility modifier may be any entity capable of effecting a particular mobility of a probe/mobility-modifier complex 80 in a mobility-dependent analysis technique. Preferably, the tail portion 60 of the mobility modifier 50 of the invention should (1) have a low polydispersity in order to effect a well-defined and easily resolved mobility, e.g., Mw/Mn less than 1.05; (2) be soluble in an aqueous medium; (3) not adversely affect probe-target hybridization or tag-tag complement binding; and (4) be available in sets such that members of different sets impart distinguishable mobilities to their associated probe/mobility-modifier complexes.

In a particularly preferred embodiment of the present invention, the tail portion of the mobility modifier comprises a polymer. Specifically, the polymer forming the tail may be homopolymer, random copolymer, or block copolymer. Furthermore, the polymer may have a linear, comb, branched, or dendritic architecture. In addition, although the invention is described herein with respect to a single polymer chain attached to an associated mobility modifier at a single point, the invention also contemplates mobility modifiers comprising more than one polymer chain element, where the elements collectively form a tail portion.

Preferred polymers for use in the present invention are hydrophilic, or at least sufficiently hydrophilic when bound to a tag complement to ensure that the tag complement is readily soluble in aqueous medium. The polymer should also not affect the hybridization between a target nucleic acid sequence and the target-specific portion of a probe associated with the mobility modifier. Where the probe is charged, as in the case of a polynucleotide probe, and the mobility-dependent analysis technique is electrophoresis, the polymers are preferably uncharged or have a charge/subunit density which is substantially less than that of the probe.

In one preferred embodiment, the polymer is polyethylene oxide (PEO), e.g., formed from one or more hexaethylene oxide (HEO) units, where the HEO units are joined end-to-end to form an unbroken chain of ethylene oxide subunits. Other exemplary embodiments include a chain composed of N 12mer PEO units, and a chain composed of N tetrapeptide units, where N is an adjustable integer (e.g., Grossman et al., U.S. Pat. No. 5,777,096).

Clearly, the synthesis of polymers useful as tail portions of a mobility modifier of the present invention will depend on the nature of the polymer. Methods for preparing suitable polymers generally follow well known polymer subunit synthesis methods. Methods of forming selected-length PEO chains are discussed below. These methods, which involve coupling of defined-size, multi-subunit polymer units to one another, either directly or through charged or uncharged linking groups, are generally applicable to a wide variety of polymers, such as polyethylene oxide, polyglycolic acid, polylactic acid, polyurethane polymers, polypeptides, and oligosaccharides. Such methods of polymer unit coupling are also suitable for synthesizing selected-length copolymers, e.g., copolymers of polyethylene oxide units alternating with polypropylene units. Polypeptides of selected lengths and amino acid composition, either homopolymer or mixed polymer, can be synthesized by standard solid-phase methods (e.g., Fields and Noble, *Int. J. Peptide Protein Res.*, 35: 161–214 (1990)).

In one preferred method for preparing PEO polymer chains having a selected number of HEO units, an HEO unit is protected at one end with dimethoxytrityl (DMT), and activated at its other end with methane sulfonate. The activated HEO is then reacted with a second DMT-protected HEO group to form a DMT-protected HEO dimer. This unit-addition is then carried out successively until a desired PEO chain length is achieved (e.g., Levenson et al., U.S. Pat. No. 4,914,210).

Another particularly preferred polymer for use as a tail portion is PNA. The advantages, properties and synthesis of PNA have been described above. In particular, when used in the context of a mobility-dependent analysis technique comprising an electrophoretic separation in free solution, PNA has the advantageous property of being essentially uncharged.

Coupling of the polymer tails to a polynucleotide tag complement can be carried out by an extension of conventional phosphoramidite polynucleotide synthesis methods, or by other standard coupling methods, e.g., a bis-urethane tolyl-linked polymer chain may be linked to an polynucleotide on a solid support via a phosphoramidite coupling. Alternatively, the polymer chain can be built up on a polynucleotide (or other tag portion) by stepwise addition of polymer-chain units to the polynucleotide, e.g., using standard solid-phase polymer synthesis methods.

As noted above, the tail portion 60 of the mobility modifier imparts a mobility to a probe/mobility modifier complex that is distinctive for each different probe/mobility modifier complex. The contribution of the tail to the mobility of the complex will in general depend on the size of the tail. However, addition of charged groups to the tail, e.g., charged linking groups in the PEO chain, or charged amino acids in a polypeptide chain, can also be used to achieve selected mobility characteristics in the probe/mobility modifier complex. It will also be appreciated that the mobility of a probe/mobility modifier complex may be influenced by the properties of the probe itself, e.g., in electrophoresis in a sieving medium, a larger probe will reduce the electrophoretic mobility of the probe/mobility modifier complex.

The tag complement portion 55 of a mobility modifier 50 according to the present invention may be any entity capable of binding to, and forming a complex with, a tag portion 15 of a probe 5. The structure and properties of the tag complement are essentially the same as those discussed above with respect to the tag portion 15 of the probe 5. Furthermore, the tag-complement portion of the mobility modifier may be attached to the tail portion using conventional means substantially as described above with respect to the attachment of the tag to the probe.

When a tag complement is a polynucleotide, e.g., PNA, the tag complement may comprise all, part, or none of the tail portion of the mobility modifier. In some embodiments of the invention, the tag complement may consist of some or all of the tail portion of the mobility modifier. In other embodiments of the invention, the tag complement does not comprise any portion of the tail portion of the mobility modifier. For example, because PNA is uncharged, particularly when using free solution electrophoresis as the mobility-dependent analysis technique, the same PNA oligomer may act as both a tag complement and a tail portion of a mobility modifier.

In a preferred embodiment of the binary composition according to the present invention, a member of the binary composition includes a hybridization enhancer. In certain circumstances, using a hybridization enhancer allows for shorter target-specific portions to be used, thereby increasing the sensitivity of a probe to single-base mismatches between the probe and target nucleic acid sequence. The hybridization enhancer may be attached to any portion of a probe or mobility modifier, so long as it is attached to the probe or mobility modifier is such a way as to allow interaction with a target-probe duplex. However, preferably, the hybridization enhancer is covalently attached to a probe of the binary composition. A particularly preferred hybridization enhancer for use in the present invention is minor-groove binder, e.g., netropsin, distamycin, and the like.

In another preferred embodiment, a member of the binary composition includes a label. Labels may be attached using well known techniques (e.g., Hermanson, *Bioconjugate Techniques*, Academic Press (1996)). Particularly preferred labels include fluorescent dyes.

III. Sequence Detection Methods

The practice of the methods of the present invention will utilize, unless otherwise indicated, standard techniques of molecular biology, which are within the skill of the art.

In one aspect, the present invention provides a method for detecting one or more target nucleic acid sequences present in a sample. The method is generally performed as follows. A sample potentially containing one or more target nucleic acid sequences is contacted with a probe comprising a target-specific portion for sequence-specific binding to the target nucleic acid sequence and a tag, under conditions suitable for sequence-dependent binding of the probe and the target nucleic acid sequence, e.g., Watson-Crick or Hoogstien binding. A mobility modifier comprising a tag complement for binding to the tag is contacted with the probe, under conditions suitable for binding the tag to the tag complement, thereby forming a probe/mobility modifier complex. The probe/mobility modifier complex is then treated to form a modified probe, e.g., a labeled nucleotide terminator is enzymatically added to a 3'- end of the probe thereby extending the probe by one nucleotide and labeling the probe. Finally, the probe/mobility modifier complex is analyzed using a mobility-dependent analysis technique. Clearly, it will be understood by one of ordinary skill in the molecular biology art that the order of the steps of the method is not critical to the invention, e.g., the probe may be treated before or after the probe/mobility modifier complex is formed.

The conditions necessary to effect sequence-specific probe-target binding depend upon the nature of the target-specific portion of the probe, and the nature of the target nucleic acid sequence, e.g., is the target nucleic acid sequence in a single- or double-stranded form. Preferably, conditions are chosen such that single nucleotide variations in the target nucleic acid sequences are detectable. Generally, conditions should be chosen to obtain a balance between specificity of probe annealing, i.e., the frequency with which an undesired nucleic acid sequence participates in a binding event with the probe, and efficiency of binding, i.e., the extent to which a desired target nucleic acid sequence participates in a binding reaction with a probe.

When the target-specific portion of a probe is a polynucleotide, specificity of probe annealing is generally controlled by the length of the target-specific portion of the probe, the solvent conditions, e.g., salt concentration, and the temperature of the annealing, or hybridization, reaction. Typically, polynucleotides between about 10 and 30 nucleotides are preferred because such polynucleotides tend to be very sequence specific when the annealing temperature is set within a few degrees of a probe melting temperature (e.g., Dieffenbach et al., *PCR Primer: A Laboratory Manual*, Dieffenbach and Dveksler, eds., p 133–142, CSHL Press, New York (1995)). Other factors that will influence the characteristics of the hybridization interaction include the GC content of the probe and target sequence and the presence of hybridization enhancers. A number of computer programs are available to facilitate selection of target-specific portions of probes in different contexts (e.g., Osborne, *CABIOS*, 8: 83 (1991); Montpetit et al., *J. Virol. Methods*, 36: 119–128 (1992)).

Following probe binding to the target nucleic acid sequence, e.g., by polynucleotide hybridization, the probes may be treated to selectively modify probes that have bound to the target nucleic acid sequences in a sequence-specific manner. Such selective modification serves to indicate when and where a target specific binding event has occurred, and may serve to provide additional information regarding the target nucleic acid sequence beyond that gleaned from simple probe hybridization. Several alternative modification methods are available depending on the nature of the probe (e.g., Grossman et al., U.S. Pat. No. 5,777,096).

In one preferred modification method, a polynucleotide probe is joined by ligation to a second polynucleotide, e.g., by chemical, photo-chemical or enzymatic ligation (e.g., Landegren et al., *Science*, 241: 1077–1080 (1988); Whiteley, U.S. Pat. No. 5,521,065; Baron et al., *Nature Biotechnology*, 14: 1279–1282 (1996); Barany, *Proc. Natl. Acac. Sci. USA*, 88: 189–193 (1991)). In a particularly preferred embodiment of this ligation modification step, the ligation junction is located across an expected single-base polymorphism, e.g, a single-base mutation site. In another preferred embodiment, the second polynucleotide includes a label such that only probes that have been ligated to a second polynucleotide become labeled. Signal amplification can be achieved by thermocycling the ligation reaction, e.g., a LAR reaction.

In another preferred modification method, one or more probes are extended in a polymerase-mediated primer extension reaction in the presence of a primer extension reagent (e.g., Mullis, U.S. Pat. No. 4,683,202; Sanger and Coulson, *Proc. Natl. Acad. Sci. USA*, 74: 5463–5467 (1977)). In a particularly preferred version of this embodiment, known generally as minisequencing, or single nucleotide extension (SNE), the primer extension reagent does not contain any chain-extension nucleotides, but rather contains one or more chain-terminating nucleotides, e.g., dideoxynucleotide terminators (e.g., Syvanen et al., *Genomics*, 8: 684–692 (1990); Soderlund and Syvanen, PCT Patent Application No. WO 91/13075; Goelet et al., PCT Patent Application No. WO 92/15712) Thus, the probes are extended by only a single nucleotide, and the identity of that nucleotide provides information about the target sequence immediately adjacent to the 3'- end of the probe. More preferably, the chain-terminating nucleotide is labeled with a label capable of determining the identity of the nucleotide, e.g., whether the nucleotide is an A, G, C or T nucleotide, e.g., by attaching a fluorescent label to the nucleotide.

In yet another preferred modification method, the probe is modified by the enzymatic cleavage, e.g., cleavage by RNaseH endonuclease, and/or activation of a cleavable probe bound to a target region (e.g., Duck et al., *Biotechniques*, 9(2): 147–152 (1990); Duck et al., U.S. Pat. No. 5,011,769; U.S. Pat. No. 5,792,607).

To effect formation of a probe/mobility modifier complex, the probe and the mobility modifier arc contacted under conditions such that the tag portion of the probe and the tag complement portion of the mobility modifier bind in a specific manner to form a stable complex. Methods and conditions used to effect the formation of the probe/mobility modifier complex will depend on the nature of the tag and tag complement portions of the probe and mobility modifier as described above. In a particularly preferred embodiment of the present invention, the tag is a conventional polynucleotide and the tag complement is PNA, where the PNA binds to the polynucleotide tag in a duplex or triplex configuration, and the binding conditions are chosen such that the PNA and conventional polynucleotide form a stable and sequence-specific bond (e.g., Perry-O'Keefe et al., *Proc. Natl. Acad. Sci USA*, (93: 14670–14675 (1996)).

In another preferred embodiment, both the tag and tag complement are conventional polynucleotide, and after formation of the probe/mobility modifier complex, the duplex formed by the tag and tag complement is cross-linked using conventional chemical or photochemical nucleic acid crosslinking techniques (e.g., Meyer et al., *J. Amer. Cheer. Soc.*, 111:8517–19 (1989); Pieles et al., *Nucleic Acids Res.*, 13:2399–2412 (1989); Praseuth et al., *Proc. Natl. Acad. Sci. USA*, 85:1349–53 (1988)). To avoid crosslinking the probe to the target nucleic acid, the tag/tag complement crosslinking reaction is preferably performed when the probe and target are not hybridized to one another.

In a particularly preferred embodiment of the invention, a plurality of probes is directed against a plurality of target nucleic acid sequences, where each probe includes a unique tag portion, specific for a tag complement portion of a particular mobility modifier. A plurality of mobility modifiers may be contacted with the probes, where each mobility modifier includes a tag complement directed towards a particular tag. Therefore, a plurality of probe/mobility modifier complexes are formed in a single step.

According to an important feature of the invention, a plurality of probe/mobility modifier complexes are resolved via a mobility-dependent analysis technique. One advantage of this feature is that probes used in the method can be designed to have similar sizes and therefore exhibit substantially the same hybridization kinetics, while being easily resolved in a mobility-dependent analysis technique.

In one embodiment of the invention, probes are resolved (separated) by liquid chromatography. Exemplary stationary phase media for use in the method include reversed-phase media (e.g., C-18 or C-8 solid phases), ion-exchange media (particularly anion-exchange media), and hydrophobic interaction media. In a related embodiment, the probes can be separated by micellar electrokinetic capillary chromatography (MECC).

Reversed-phase chromatography is carried out using an isocratic, or more typically, a linear, curved, or stepped solvent gradient, wherein the level of a nonpolar solvent such as acetonitrile or isopropanol in aqueous solvent is increased during a chromatographic run, causing analytes to elute sequentially according to affinity of each analyte for the solid phase. For separating polynucleotides, an ion-pairing agent (e.g., a tetra-alkylammonium) is typically included in the solvent to mask the charge of phosphate.

The mobility of a probe can be varied by attachment to mobility modifiers comprising polymer chains that alter the affinity of the probe for the solid, or stationary, phase. Thus, with reversed phase chromatography, an increased affinity of the probe for the stationary phase can be attained by addition of a moderately hydrophobic tail (e.g., PEO-containing polymers, short polypeptides, and the like) to the probe. Longer tails impart greater affinity for the solid phase, and thus require higher non-polar solvent concentration for the probe to be eluted (and a longer elution time).

Generally, in anion-exchange chromatography, analytes are eluted from a positively charged stationary phase using a salt gradient, where analytes elute according to the number and distribution of negative charges in each analyte. As polyanions, polynucleotides elute according to the length of the polynucleotide, with the smallest polynucleotides eluting first, and longer polynucleotides eluting as the concentration of salt is increased over time. Thus, where anion exchange chromatography is used in the method of the invention, the mobility modifiers attached to the probes may be charged; positively charged tails can be used to reduce the affinity of a probe for the solid phase, and negatively charged tails can be used to increase affinity for the solid phase. Similar considerations apply to hydrophobic interaction chromatography.

In micellar electrokinetic capillary chromatography (MECC), polynucleotides may separate by electrophoretic passage through a separation medium that contains micelles formed by surfactant molecules (e.g., sodium dodecyl sulfate). Sample separation is mediated by partitioning of the sample components between a primary phase, formed by the running buffer, and a secondary phase, formed by micelles, in a separation process that may be characterized as a form of chromatography. For enhanced polynucleotide separation, the separation medium may contain divalent metal ions, for complexing with sample polynucleotides to modify polynucleotide mobilities.

According to a particularly preferred embodiment of the present invention, the probe/mobility modifier complexes are resolved by electrophoresis in a sieving or non-sieving matrix. Preferably, the electrophoretic separation is carried out in a capillary tube by capillary electrophoresis (e.g., *Capillary Electrophoresis: Theory and Practice*, Grossman and Colburn eds., Academic Press (1992)). Preferred sieving matrices which can be used include covalently crosslinked matrices, such as polyacrylamide covalently crosslinked with bis-acrylamide; gel matrices formed with linear polymers (e.g., Madabhushi et al. U.S. Pat. No. 5,552,028); and gel-free sieving media (e.g., Grossman et al., U.S. Pat. No. 5,624,800; Hubert and Slater, *Electrophoresis*, 16: 2137–2142 (1995); Mayer et al., *Analytical Chemistry*, 66(10): 1777–1780 (1994)). The electrophoresis medium may contain a nucleic acid denaturant, such as 7M formamide, for maintaining polynucleotides in single stranded form. Suitable capillary electrophoresis instrumentation are commercially available, e.g., the ABI PRISM™ Genetic Analyzer (PE Biosystems, Foster City, Calif.).

To facilitate detection, an element of the binary compositions of the invention may contain, or can be modified to contain, a label which allows direct detection of a labeled element by a suitable detector. Preferably, the label is a fluorescent label which, more preferably, is spectrally resolvable from other fluorescent labels in a set. For example, the reporter label may be attached to the 5' or 3'-terminal base of the polynucleotide portion of the probe, by methods well known in the nucleotide chemistry art (e.g., Fung et al, U.S. Pat. No. 4,855,225; Prober et al, *Science* 238, 4767–4771 (1987); Smith et al., *Nucleic Acids Res.* 13, 2399–2412 (1985)).

Exemplary fluorescent labels include the dyes 5- and 6-carboxyfluorescein, 5- and 6-carboxy-4,7-dichlorofluorscein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8'-dibenzo-4',5'-dichloro-5- and 6-carboxy-4,7-dichlorofluorescein, 2',7'-dichloro-5- and 6-carboxy-4,7-dichlorofluorescein, and 2',4', 5',7'-tetrachloro-5- and 6-carboxy-4,7-dichlorofluorescein. The above-mentioned dyes are disclosed elsewhere (e.g., Hobbs, Jr., U.S. Pat. No. 4,997,928; Fung et al, U.S. Pat. No. 4,855,225; and Menchen et al, U.S. Pat. No. 5,188,934) Alternatively, probes of the invention may be labeled with spectrally resolvable rhodamine dyes (e.g., Bergot et al, U.S. Pat. No. 5,366,860). A particularly preferred class of dyes useful in the present invention comprise fluorescent energy transfer dyes (e.g., Lee et al., U.S. Pat. No. 5,800,996; Lee et al., *Nucleic Acids Research*, 25 (14): 2816–2822 (1997)).

Figure 4A:
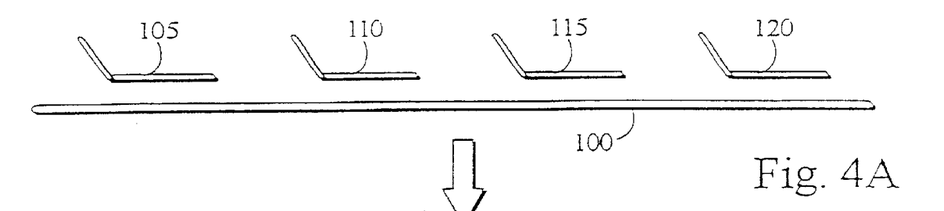
FIGS. 4A, 4B, 4C and 4D show various stages of a schematic representation of a preferred method according to the present invention.
Figure 4B:
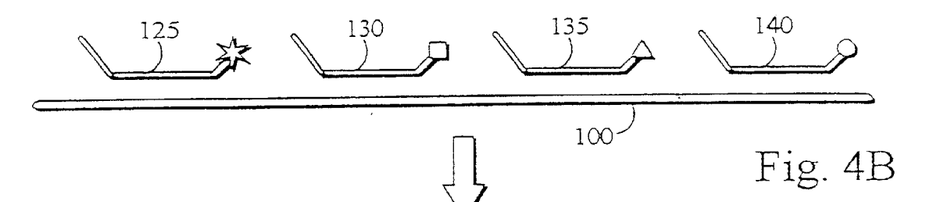
Figure 4C:
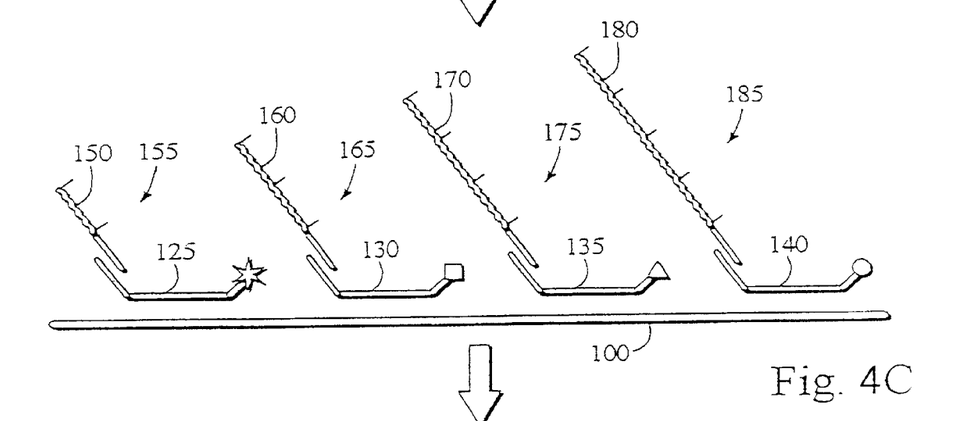
Figure 4D:
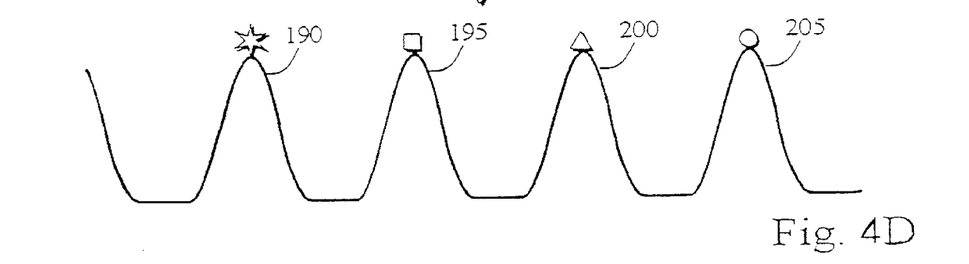

An exemplary preferred embodiment of a method according to the present invention is schematically depicted in FIGS. 4A, 4B, 4C and 4D. In FIG. 4A, four polynucleotide probes 105, 110, 115 and 120 are hybridized to a target nucleic acid sequence 100 in a single reaction mixture under conditions suitable for sequence-specific hybridization. Next, in FIG. 4B, the hybridized, or bound, probes are modified to form modified probes 125, 130, 135 and 140. For example, the modification step may comprise a single-nucleotide primer extension reaction, i.e., a mini-sequencing reaction, in which the added nucleotide terminator is labeled with a distinguishable label, e.g., a spectrally-resolvable fluorescent label, or a ligation reaction, where the second polynucleotide contains a distinguishable label. Next, in FIG. 4C, the modified probes 125, 130, 135 and 140 are contacted with their associated mobility modifiers 150, 160, 170 and 180, respectively, to form probe/mobility modifier complexes 155, 165, 175 and 185, where each probe is associated with a mobility modifier having a particular size that results in a different mobility address for each probe/ mobility modifier complex. Finally, in FIG. 4D, the probe/ mobility modifier complexes 155, 165, 175 and 185 are resolved using a mobility-dependent analysis technique, e.g., capillary electrophoresis in a sieving or non-sieving medium, resulting in an electropherogram including peaks 190, 195, 200 and 205 corresponding to probe/mobility modifier complexes 155, 165, 175 and 185, respectively.

In the above example, each probe was resolved to a separate mobility address. However, it will be realized that, in order to conserve mobility addresses, it may be desirable in some circumstance to place several probes at the same mobility address, and distinguish the probes within each address by a distinguishable label, e.g., spectrally-resolvable fluorescent labels.

It will be appreciated that a particularly attractive feature of the methods and binary compositions of the present invention is that a single set of mobility modifiers can be used with different sets of target-specific probes, thereby greatly reducing the number of tailed entities that must be synthesized.

In one exemplary system, 10,000 biallelic SNP loci are interrogated using 100 mobility modifiers and 10,000 unlabeled and untailed polynucleotide probes. The system comprises 100 different mobility modifiers, each mobility modifier having a distinguishable tag complement and a distinguishable mobility when part of a probe/mobility modifier complex. The system further comprises 100 sets of probes, each set comprising 100 individual probes, where each probe comprises a distinguishable tag portion, and each set of probes is located in a separate reaction tube. An aliquot of a sample containing a target nucleic acid comprising a possible 20,000 target nucleic acid sequences is added to each reaction tube of the 100 tube collection of tubes, i.e., each of the two alleles of the 10,000 loci. Using a multiplex PCR, each of the target sequences is amplified. Then, in each tube, the probes and the amplified target nucleic acids are contacted under conditions effective for sequence-dependent hybridization. Next, the hybridized probes are modified by conducting a minisequencing reaction using fluorescently-labeled nucleotide terminator, where each of the A, G, C and T terminators are labeled with a spectrally resolvable fluorescent label. Next, to each of the 100 reaction tubes is added the same collection of 100 mobility modifiers. Then, each tube is separately analyzed using a mobility-dependent analysis technique such that a color is associated with each mobility address, e.g., each tube is simultaneously analyzed by electrophoresis using a multicapillary capillary electrophoresis system, e.g., ABI PRISM™ Model 3700 Genetic Analyzer (PE Biosystems, Foster City, Calif.). Note that in the context of the present invention, a mobility address may be based on an absolute value of an electrophoretic mobility or a relative electrophoretic mobility based on an internal or external standard. Finally, the resulting color-mobility address data are compared with a base-line data set stored in a computer and a genotype of the sample is determined. Thus, in this exemplary embodiment, while 100×100 (10,000) different probes are required, i.e., one probe for each locus-specific target nucleic acid sequence, only 100 different mobility modifiers are required. And, in an example such as this where the modification step serves to label the probes and to provide additional sequence information, i.e., the identity of a nucleotide immediately adjacent to a probe's 3'-end, none of the 10,000 probes need to be labeled beforehand. Therefore, as this example demonstrates, using the methods and compositions of the present invention, to create an assay capable of interrogating 40,000 different target sequences, e.g., 10,000 SNP loci, one need only to make 100 different mobility modifiers and 10,000 unlabeled and untailed probes.

Of course, each of the above sets may be automated using a computer-controlled X-Y-Z laboratory robot, e.g., the BioMek from Beckman Instruments, used in combination with a high-throughput capillary electrophoresis device, e.g., the ABI PRISM™ 3700 DNA Analyzer from PE Biosystems.

All publications and patent applications are herein incorporated by reference to the same extent as if each individual publication or patent application was specifically, expressly and individually indicated to be incorporated by reference when first cited.

Although only a few embodiments have been described in detail above, those having ordinary skill in the molecular biology art will clearly understand that many modifications are possible in the preferred embodiment without departing from the teachings and spirit thereof. All such modifications are intended to be encompassed within the following claims.

I claim:

1. A method for detecting one or more target nucleic acid sequences present in a sample comprising:

providing a sample potentially containing one or more target nucleic acid sequences;

providing one or more probes, each probe comprising a target-specific portion and a tag;

providing one or more mobility-modifiers, each mobility modifier comprising a tag complement and a tail;

contacting the probe(s) and the target nucleic acid sequence(s) under conditions effective for sequence-dependent hybridization of the probe(s) and the target nucleic acid sequence(s), thereby forming a bound probe(s);

treating the bound probe(s) to form a modified probe(s);

contacting the probe(s), the bound probe(s) or the modified probe(s) and the mobility-modifier(s) under conditions suitable for selectively binding the tag(s) and the tag complement(s), thereby forming one or more probe/mobility modifier complex(s); and analyzing the probe/mobility modifier complex(s) using a mobility-dependent analysis technique under conditions that do not disrupt the probe/mobility modifier complex.

2. The method of claim 1 wherein the step of treating the bound probe comprises a ligation reaction.

3. The method of claim 1 wherein the step of treating the bound probe comprises a primer extension reaction.

4. The method of claim 1 wherein the step of treating the bound probe comprises attaching a label to the probe.

5. The method of claim 1 wherein the target-specific portion comprises polynucleotide.

6. The method of claim 5 wherein the target-specific portion comprises a 3'-hydroxyl group.

7. The method of claim 5 wherein the target-specific portion comprises PNA.

8. The method of claim 1 wherein the tag complement portion comprises polynucleotide.

9. The method of claim 8 wherein the tag complement portion is PNA.

10. The method of claim 1 wherein both the tag and tag complement are polynucleotide, and one of the tag complement and tag comprises the sequence $(CAG)_n$ wherein n is 1 to 10.

11. The method of claim 1 wherein the tail is a polymer.

12. The method of claim 11 wherein the polymer is selected from the group consisting of polyethyleneoxide and polypeptide.

13. The method of claim 1 further comprising a hybridization enhancer.

14. The method of claim 1 wherein two or more probes and two or more mobility modifiers are provided such that each probe selectively binds to a mobility modifier, thereby forming a probe/mobility modifier complex, wherein at least two of the probe/mobility modifier complexes are resolvable in the mobility-dependent analysis technique.

* * * * *